(12) United States Patent
Crawford et al.

(10) Patent No.: US 8,515,112 B2
(45) Date of Patent: Aug. 20, 2013

(54) MODULAR SPEECH PROCESSOR HEADPIECE

(75) Inventors: Scott A. Crawford, Castaic, CA (US); Douglas P. Lynch, Shepherdstown, WV (US); Carla Mann Woods, Beverly Hills, CA (US)

(73) Assignee: Advanced Bionics, LLC, Valencia, CA (US)

( * ) Notice: Subject to any disclaimer, the term of this patent is extended or adjusted under 35 U.S.C. 154(b) by 0 days.

(21) Appl. No.: 13/601,992

(22) Filed: Aug. 31, 2012

(65) Prior Publication Data

US 2012/0330378 A1 Dec. 27, 2012

Related U.S. Application Data

(63) Continuation of application No. 12/397,982, filed on Mar. 4, 2009, now Pat. No. 8,270,647.

(60) Provisional application No. 61/113,708, filed on Nov. 12, 2008.

(51) Int. Cl.
  *H04R 25/00* (2006.01)
(52) U.S. Cl.
  USPC ........... 381/326; 181/129; 181/135; 381/314; 381/315; 381/323; 381/324; 600/25; 607/57
(58) Field of Classification Search
  USPC ................. 381/314, 315, 323, 324, 326, 328; 600/25; 607/55–57
  See application file for complete search history.

(56) References Cited

U.S. PATENT DOCUMENTS

| 2,975,226 A | 3/1961 | Lehr |
| 3,055,990 A | 9/1962 | Sidlo |
| 3,942,535 A | 3/1976 | Schulman |

(Continued)

FOREIGN PATENT DOCUMENTS

| WO | WO 9837926 A1 | 9/1998 |
| WO | WO 0139830 A2 | 6/2001 |

(Continued)

OTHER PUBLICATIONS

"Adjustable Strength Magnet System for a Cochlear Implant Headpiece"; IP.com Publication; IPCOM000010043D; (Oct. 2002).

(Continued)

*Primary Examiner* — Allan R Wilson
(74) *Attorney, Agent, or Firm* — Henricks, Slavin & Holmes LLP

(57) ABSTRACT

A cochlear implant system includes: an electrode array implanted within a cochlea; an internal processor in communication with the electrode array; an implanted antenna which is electrically coupled to the internal processor; and a modular external headpiece which is removably positioned over the implanted antenna, the modular external headpiece including a core containing a sound processor for processing sound and providing a corresponding signal to the implanted antenna; and a modular component configured to releasably engage the core and supply electrical power to the core. A modular speech processor headpiece includes a core comprising a microphone and sound processor for producing a signal representing ambient sound to be transmitted to a cochlear implant, the core further comprising a number of electrical contacts; and a modular component containing a number of electrical contacts corresponding to the electrical contacts of the core; wherein the core is configured to engage with the modular component such that electrical communication is made between the core and the modular component.

23 Claims, 7 Drawing Sheets

(56) References Cited

U.S. PATENT DOCUMENTS

| | | |
|---|---|---|
| 4,006,748 A | 2/1977 | Schulman |
| 4,041,955 A | 8/1977 | Kelly et al. |
| 4,134,408 A | 1/1979 | Brownlee et al. |
| 4,352,960 A | 10/1982 | Dormer et al. |
| 4,379,988 A | 4/1983 | Mattatall |
| 4,532,930 A | 8/1985 | Crosby et al. |
| 4,592,359 A | 6/1986 | Galbraith |
| 4,918,736 A | 4/1990 | Bordewijk et al. |
| 4,947,439 A | 8/1990 | Buettner et al. |
| 5,279,292 A | 1/1994 | Baumann et al. |
| 5,314,451 A | 5/1994 | Mulier |
| 5,411,537 A | 5/1995 | Munshi et al. |
| 5,411,538 A | 5/1995 | Lin |
| 5,522,865 A | 6/1996 | Schulman et al. |
| 5,571,148 A | 11/1996 | Loeb et al. |
| 5,603,726 A | 2/1997 | Schulman et al. |
| 5,610,494 A | 3/1997 | Grosfilley et al. |
| 5,626,629 A | 5/1997 | Faltys et al. |
| 5,702,431 A | 12/1997 | Wang et al. |
| 5,824,022 A | 10/1998 | Zilberman et al. |
| 5,906,635 A | 5/1999 | Maniglia |
| 5,948,006 A | 9/1999 | Mann |
| 5,949,895 A | 9/1999 | Ball et al. |
| 6,067,474 A | 5/2000 | Schulman et al. |
| 6,129,753 A | 10/2000 | Kuzma et al. |
| 6,190,305 B1 | 2/2001 | Ball et al. |
| 6,219,580 B1 | 4/2001 | Faltys et al. |
| 6,246,911 B1 | 6/2001 | Seligman |
| 6,249,704 B1 | 6/2001 | Maltan |
| 6,265,100 B1 | 7/2001 | Saaski et al. |
| 6,272,382 B1 | 8/2001 | Faltys et al. |
| 6,275,736 B1 | 8/2001 | Kuzma et al. |
| 6,275,737 B1 | 8/2001 | Mann |
| 6,289,247 B1 | 9/2001 | Faltys et al. |
| 6,304,787 B1 | 10/2001 | Kuzma et al. |
| 6,308,101 B1 | 10/2001 | Faltys et al. |
| 6,310,960 B1 | 10/2001 | Saaski et al. |
| 6,358,281 B1 | 3/2002 | Berrang et al. |
| 6,394,947 B1 | 5/2002 | Leysieffer |
| 6,415,185 B1 | 7/2002 | Maltan |
| 6,434,429 B1 | 8/2002 | Kraus et al. |
| 6,473,511 B1 | 10/2002 | Aceti et al. |
| 6,496,734 B1 | 12/2002 | Money |
| 6,556,870 B2 | 4/2003 | Zierhofer et al. |
| 6,560,488 B1 | 5/2003 | Crawford |
| 6,648,914 B2 | 11/2003 | Berrang et al. |
| 6,658,124 B1 | 12/2003 | Meadows |
| 6,726,618 B2 | 4/2004 | Miller |
| 6,786,806 B2 | 9/2004 | Maus, Jr. |
| 6,786,860 B2 | 9/2004 | Maltan et al. |
| 6,807,445 B2 | 10/2004 | Baumann et al. |
| 6,842,647 B1 | 1/2005 | Griffith |
| 6,862,805 B2 | 3/2005 | Kuzma et al. |
| 6,879,695 B2 | 4/2005 | Maltan |
| 6,879,855 B2 | 4/2005 | Schulman et al. |
| 7,043,303 B1 | 5/2006 | Overstreet |
| 7,054,691 B1 | 5/2006 | Kuzma et al. |
| 7,149,551 B2 | 12/2006 | Kim |
| 7,174,214 B2 | 2/2007 | Seligman |
| 7,266,208 B2 | 9/2007 | Charvin et al. |
| 7,266,209 B1 | 9/2007 | House |
| 7,292,880 B2 | 11/2007 | Lehtonen |
| 7,349,741 B2 | 3/2008 | Maltan et al. |
| 7,386,143 B2 | 6/2008 | Easter et al. |
| 7,599,508 B1 | 10/2009 | Lynch et al. |
| 7,848,817 B2 | 12/2010 | Janzig et al. |
| 7,945,334 B2 | 5/2011 | Jimenez et al. |
| 8,107,661 B1 | 1/2012 | Lynch et al. |
| 8,140,168 B2 * | 3/2012 | Olson et al. ............ 607/61 |
| 8,170,253 B1 | 5/2012 | Lynch et al. |
| 8,270,647 B2 | 9/2012 | Crawford et al. |
| 8,280,524 B2 | 10/2012 | Duftner et al. |
| 8,340,774 B2 * | 12/2012 | Hochmair et al. ............ 607/57 |
| 8,352,037 B2 * | 1/2013 | Darley et al. ............ 607/57 |
| 2002/0019669 A1 | 2/2002 | Berrang et al. |
| 2002/0032472 A1 | 3/2002 | Zarinetchi et al. |
| 2002/0076071 A1 | 6/2002 | Single |
| 2002/0120332 A1 | 8/2002 | Law |
| 2003/0086583 A1 | 5/2003 | Maltan et al. |
| 2004/0073275 A1 | 4/2004 | Maltan et al. |
| 2004/0133065 A1 | 7/2004 | Easter et al. |
| 2004/0202339 A1 | 10/2004 | O'Brien |
| 2004/0249428 A1 | 12/2004 | Wang et al. |
| 2005/0113888 A1 | 5/2005 | Jimenez et al. |
| 2005/0159791 A1 | 7/2005 | Daly et al. |
| 2005/0245991 A1 | 11/2005 | Faltys et al. |
| 2005/0251225 A1 | 11/2005 | Faltys et al. |
| 2005/0267549 A1 | 12/2005 | Della Santina et al. |
| 2006/0015155 A1 | 1/2006 | Charvin |
| 2006/0030905 A1 * | 2/2006 | Medina Malaver ............ 607/61 |
| 2006/0052841 A1 | 3/2006 | Daly et al. |
| 2006/0184212 A1 | 8/2006 | Faltys et al. |
| 2006/0190059 A1 | 8/2006 | Griffith |
| 2007/0053534 A1 | 3/2007 | Kiratzidis |
| 2007/0055321 A1 | 3/2007 | Gordon et al. |
| 2007/0104342 A1 | 5/2007 | Seligman |
| 2007/0106345 A1 | 5/2007 | Seligman |
| 2007/0191673 A1 | 8/2007 | Ball et al. |
| 2007/0282394 A1 | 12/2007 | Segel et al. |
| 2008/0002834 A1 | 1/2008 | Hochmair |
| 2008/0228243 A1 | 9/2008 | Maltan et al. |
| 2009/0005836 A1 | 1/2009 | Chang et al. |
| 2009/0177247 A1 | 7/2009 | Neal et al. |
| 2010/0036458 A1 | 2/2010 | Duftner et al. |
| 2010/0046778 A1 | 2/2010 | Crawford et al. |
| 2010/0046779 A1 | 2/2010 | Crawford et al. |
| 2012/0275629 A1 * | 11/2012 | Meskens et al. ............ 381/315 |

FOREIGN PATENT DOCUMENTS

| | | |
|---|---|---|
| WO | WO 0150816 A1 | 7/2001 |
| WO | WO 03030772 A2 | 4/2003 |
| WO | WO 2005062668 A1 | 7/2005 |
| WO | WO 2005110530 A2 | 11/2005 |
| WO | WO 2007124325 A2 | 11/2007 |
| WO | WO 2007146773 A1 | 12/2007 |
| WO | WO 2008010647 A1 | 1/2008 |
| WO | WO 2010017118 A1 | 2/2010 |
| WO | WO 2010056751 A1 | 5/2010 |
| WO | WO 2010056768 A1 | 5/2010 |
| WO | WO 2010056770 A1 | 5/2010 |

OTHER PUBLICATIONS

JABRA Corporation; "JABRA FreeSpeak(tm) BT200 Wireless Mobile Headset Users Manual"; JABRA Corporation of 9171 Towne Centre Drive, Suite 500, San Diego, California 92122; (2004); http://www.wirelessgalaxy.comfacfjabra/BTFS_Manual.pdf.

Qian, et al.; "A Bluetooth-Based Wireless Phone Adapter for Cochlear Implant Users"; Department of Electrical Engineering University of Texas at Dallas; http://www.utdallas.edu/~loizou/cimplants/bluetooth.pdf; Asilomar (2001).

Qian, et al.; "A Phone-Assistive Device Based on Bluetooth Technology for Cochlear Implant Users"; IEEE Transactions on Neural Systems and Rehabilitation Engineering; (Jan. 2003); pp. 282-287.

cap. (n.d.); Webster's New Miliennium™ Dictionary of English, Preview Edition (v 0.9.7); Retrieved Jan. 21, 2009; from Dictionary.com website: http://dictionary.reference.com/browse/cap.

cap; Retrieved Jan. 21, 2009; from http://www.yourdictionary.com/cap.

cap; (2009); In Merriam-Webster Online Dictionary; Retrieved Jan. 21, 2009; from http://www.merriam-webster.Comfdictionary/cap.

BionicEar.com—Harmony Cochlear Implant by Advanced Bionics; "Components of a Cochlear Implant", Jan. 21, 2009.

Welcome to Spokane Ear, Nose & Throat Clinic, P.S. Surgery Center; Retrieved Jan. 20, 2009; from http://WWW.spokaneent.com/cochlear_implants.html.

Cochlear Implant; Medical Articles of Interest from Garamchai.Com; Retrieved Jan. 20, 2009; from http://WWW.garamchai.com/DesiTrendsMedical1.htm.

Cochlear Implant Programme; Cochlear Implants, Speech Laboratory, Audiology, E . . . ; Retrieved Jan. 20, 2009; from http://WWW.kkrenthospital.org/surgery_cochlear.htm.

"Cochlear Implants Bring Identity Change"; Otolaryngology—Head and Neck Surgery; Breakthrough; Autumn 2004; p. 6.

UCSF—Cochlear Implant; "Implant System"; Retrieved Jan. 20, 2009; from http://cochlearimplant.ucsf.edu/page.asp?bodyid=implantsystem.

"Cochlear Implants and Children"; Advance for Audiologists; Sep./Oct. 2000; p. 26; WWW.advanceforAUD.com.

Cochlear implants—What is a Cochlear Implant and How Does it Work?; My Baby's Hearing; Retrieved Jan. 20, 2009; from.

House, William F.; "The All Hear Cochlear Implant System: the AliHear Device, their Manufacture, Preliminary Test Results, & the Future"; p. 1-46.

Hansaton Akustik GMBH, Product Brochures and Technical Information; Stueckenstrasse 48-D-22081, Hamburg, Germany.

Florian, John. "Technologically, cochlear implants have taken giant steps." *The Hearing Journal* vol. 56, No. 4 (Apr. 2003) pp. 48.55.

Office Action dated Dec. 27, 2011 in U.S. Appl. No. 12/398,058.

Office Action dated Jun. 5, 2015 in U.S. Appl. No. 12/398,058.

Office Action dated May 30, 2013 in U.S. Appl. No. 12/398,058.

* cited by examiner

MODULAR SPEECH PROCESSOR HEADPIECE

RELATED DOCUMENTS

The present application is a continuation of U.S. application Ser. No. 12/397,982, filed Mar. 4, 2009, now U.S. Pat. No. 8,270,647, which claims benefit under 35 U.S.C. §119(e) of U.S. Provisional Application No. 61/113,708, by Scott A. Crawford et al., filed on Nov. 12, 2008, and entitled "Modular Speech Processor Headpiece." These applications are hereby incorporated by reference in their entireties.

Additionally, U.S. application Ser. No. 12/398,058, filed Mar. 4, 2009 and entitled "Integrated Cochlear Implant Headpiece," is herein incorporated by reference in its entirety.

U.S. Provisional Application No. 61/139,567, by Glen A. Griffith, filed on Dec. 20, 2008, and entitled "Cochlear Implant Systems Including Magnetic Flux Redirection Means," discloses a telemetry flux guide and techniques for using the same to direct magnetic flux away from the circuitry in a cochlear implant. This subject matter may be used in embodiments of the devices and methods disclosed in the present application to control magnetic flux within a cochlear implant device or system. Consequently, application Ser. No. 61/139,567 is hereby incorporated by reference in its entirety.

BACKGROUND

In human hearing, hair cells in the cochlea respond to sound waves and produce corresponding auditory nerve impulses. These nerve impulses are then conducted to the brain and perceived as sound.

Hearing loss, which may be due to many different causes, is generally of two types: conductive and sensorineural. Conductive hearing loss typically occurs where the normal mechanical pathways for sound to reach the hair cells in the cochlea are impeded, for example, from damage to the ossicles. Conductive hearing loss may often be helped by using conventional hearing aids that amplify sounds so that acoustic information can reach the cochlea and the hair cells. Some types of conductive hearing loss are also amenable to alleviation by surgical procedures.

Many people who are profoundly deaf, however, have sensorineural hearing loss. This type of hearing loss can arise from the absence or the destruction of the hair cells in the cochlea which then no longer transduce acoustic signals into auditory nerve impulses. Individuals with sensorineural hearing loss may be unable to derive any meaningful benefit from conventional hearing aid systems no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural deafness, cochlear implant systems or cochlear prostheses have been developed that can bypass the hair cells located in the cochlea by presenting electrical stimulation directly to the auditory nerve fibers. This leads to the perception of sound in the brain and provides at least partial restoration of hearing function. Most of these cochlear prosthesis systems treat sensorineural deficit by stimulating the ganglion cells in the cochlea directly using an implanted electrode or lead that has an electrode array. Thus, a cochlear prosthesis operates by directly stimulating the auditory nerve cells, bypassing the defective cochlear hair cells that normally transduce acoustic energy into electrical activity to the connected auditory nerve cells.

Prior to stimulating the nerve cells, the electronic circuitry and the electrode array of the cochlear prosthesis separate acoustic signals into a number of parallel channels of information, each representing a narrow band of frequencies within the perceived audio spectrum. Ideally, each channel of information should be conveyed selectively to a subset of auditory nerve cells that normally transmit information about that frequency band to the brain. Those nerve cells are arranged in an orderly tonotopic sequence, from the highest frequencies at the basal end of the cochlear spiral to progressively lower frequencies towards the apex.

A cochlear implant system typically comprises both an external unit that receives and processes ambient sound waves and a cochlear implant that receives data from the external unit and uses that data to directly stimulate the auditory nerve. A common configuration for a cochlear implant system thus involves internal components that are surgically implanted into the patient and external components that provide power and electrical signals representing environmental sound to the internal components. These external components typically include a Behind-the-Ear (BTE) processor worn on the ear or a body worn processor. These processors contain a microphone, batteries, and signal circuitry that processes the electrical signals generated by the microphone. The processors are connected to a headpiece by a cable. The headpiece receives the electrical signals through the cable and transmits them to the internal components.

In some cochlear implant systems, the cable or cables connecting the external components together can present some issues. For example, the cable may have to be routed through clothing or accommodated during hair styling. The cable may be snagged, pulled on, or tangled, causing the headpiece to fall off. Additionally, cables are considered unattractive by many patients and are susceptible to failure due to bending.

BRIEF DESCRIPTION OF THE DRAWINGS

The accompanying drawings illustrate various embodiments of the principles described herein and are a part of the specification. The illustrated embodiments are merely examples and do not limit the scope of the claims.

Throughout the drawings, identical reference numbers designate similar, but not necessarily identical, elements.

DETAILED DESCRIPTION

Figure 1:
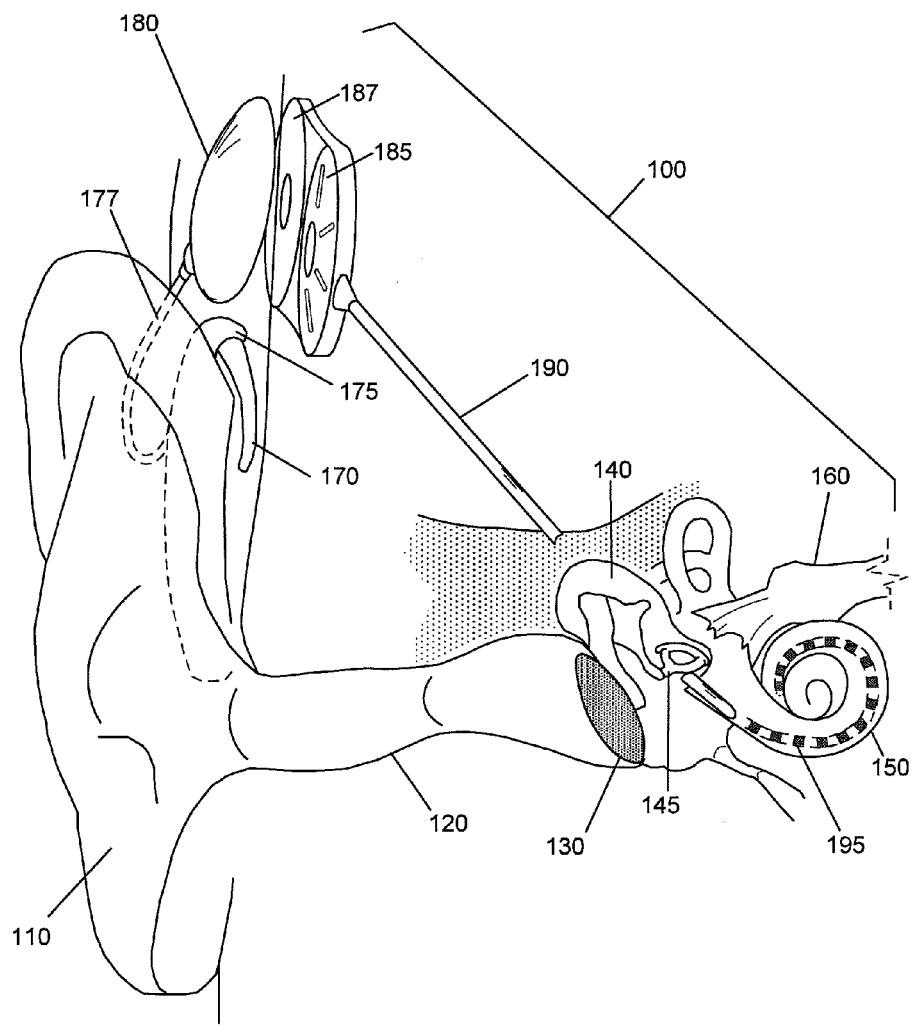
FIG. 1 is an illustrative diagram showing a cochlear implant system in use.

As mentioned above, individuals with hearing loss can be assisted by a number of hearing assistance devices. These assistive devices are typically worn regularly and over a significant period of each day. Consequently, any such hearing assistance device should be robust and reliable. Additionally, the hearing assistance devices should be visually unobtrusive and not unduly restrict the user's activities. As explained above, cochlear implant users typically must wear at least two separate external units, a processor and a headpiece, that are connected by a cable.

The processor may be a Behind-The-Ear (BTE) processor or a body worn processor. A BTE processor typically uses a hook which attaches over the top of the outer ear and holds the BTE processor in place behind the ear of the user. The BTE processor contains a microphone, battery, and electronics. A cable attaches the BTE processor to the headpiece and conveys data signals and power to the headpiece. The headpiece is typically held in place by magnetic forces generated by a surgically implanted magnet which is a part of the internal cochlear implant.

A body worn processor is typically worn by attaching the processor to an article of clothing worn by the user. For example, a body worn processor may be tucked into a pocket or attached to a lapel. The body worn processor does not have the severe size and weight constraints that are associated with a BTE processor. Consequently, the electronics and battery capacity of the body worn processor can be significantly greater than BTE processors. Like the BTE processor, a cable attaches the body worn processor to the headpiece.

As mentioned above, the cable or cables connecting the external components together can be difficult to manage. For example, when a child wears a cochlear implant, the parent may have to take additional care in dressing the child and restrict some activities the child would otherwise enjoy to prevent the cable from being snagged, pulled on, tangled, or broken. Additionally, the processor and cable can be visually distracting and are considered unattractive by many patients.

Accordingly, the present specification addresses these issues by describing a modular speech processor headpiece that combines the external components of the cochlear system into a single modular speech processor headpiece that is worn directly over the surgically implanted antenna. The modular speech processor headpiece is a head mounted, external component which provides a stand-alone support for the functionalities of the implanted components. This eliminates the need for a separate body worn processor or BTE processor and the connecting cable. Consequently, the modular speech processor headpiece reduces the complexity of wearing and using a cochlear implant. The cochlear implant system no longer requires a cable or a separate processor unit. This eliminates the need to route the cable through clothing or hair and additionally eliminates the possibility of snagging the cable. Additionally, the modular speech processor headpiece can be significantly less visually intrusive and more user friendly. The modular nature of the integrated cochlear implant headpiece may allow for other devices to communicate with and/or be attached to the integrated cochlear implant headpiece to provide additional functionality. However, the integrated headpiece is configured to provide the basic functionality for the operation of the cochlear implant as a stand alone unit.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "an embodiment," "an example," or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

Throughout the specification, a cochlear implant system which includes a Behind-The-Ear (BTE) processor and headpiece is used as an example of a typical cochlear implant system. As used in the specification and appended claims the term "headpiece" refers to a component that is worn on the user's head in proximity to an internal antenna, as opposed to a BTE processor or body worn processor.

FIG. 1 is a diagram showing one illustrative embodiment of a cochlear implant (100) which is surgically placed within the patient's auditory system. Ordinarily, sound enters the outer ear (110) and is directed into the auditory canal (120) where the sound wave vibrates the tympanic membrane (130). The motion of the tympanic membrane is amplified and transmitted through the ossicular chain (140) which consists of three bones in the middle ear. The third bone of the ossicular chain (140), the stirrup (145), contacts the outer surface of the cochlea (150) and causes movement of the fluid within the cochlea (150). Cochlear hair cells respond to the fluid-borne vibration in the cochlea (150) and trigger neural electrical signals that are conducted from the cochlea (150) to the auditory cortex by the auditory nerve (160).

As indicated above, the cochlear implant (100) is a surgically implanted electronic device that provides a sense of sound to a person who is profoundly deaf or severely hard of hearing. In many cases, deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids, which amplify external sound waves, provide no benefit to persons suffering from complete sensorineural hearing loss.

Unlike hearing aids, the cochlear implant (100) does not amplify sound, but works by directly stimulating any functioning auditory nerve cells inside the cochlea (150) with electrical impulses. Cochlear prosthesis typically involves the implantation of electrodes into the cochlea. The cochlear implant operates by direct electrical stimulation of the auditory nerve cells, bypassing the defective cochlear hair cells that normally traduce acoustic energy into electrical energy.

External components of the cochlear implant system include a BTE unit (175) which contains the speech processor and has a microphone (170), a cable (177), and a transmitter (180). The microphone (170) picks up sound from the environment and converts it into electrical impulses. The speech processor within the BTE unit (175) selectively filters and manipulates the electrical impulses and sends the processed electrical signals through a cable (177) to the transmitter (180). The transmitter (180) receives the processed electrical signals from the processor and transmits them to the antenna (187) by electromagnetic induction and/or radio frequencies.

In some cochlear implant systems, the transmitter (180) is held in place by magnetic attraction with the underlying antenna (187).

The internal components of the cochlear implant include an internal processor (185), an antenna (187), a cochlear lead (190), and electrodes array (195). The internal processor (185) and antenna (187) are secured beneath the user's skin, typically above and behind the external ear (110). The antenna (187) receives signals and power from the headpiece (180). The internal processor (185) receives these signals and performs one or more operations on the signals to generate modified signals. These modified signals are then sent through the cochlear lead (190) to the electrode array (195). The electrode array (195) is wound through the cochlea (150) and provides direct electrical stimulation to the auditory nerve inside the cochlea (150).

The cochlear implant stimulates different portions of the cochlea (150) according to the frequencies detected by the microphone (170), just as a normal functioning ear would experience stimulation at different portions of the cochlea depending on the frequency of sound vibrating the liquid within the cochlea (150). This allows the brain to interpret the frequency of the sound as if the hair cells of the basilar membrane were functioning properly.

Figure 2:
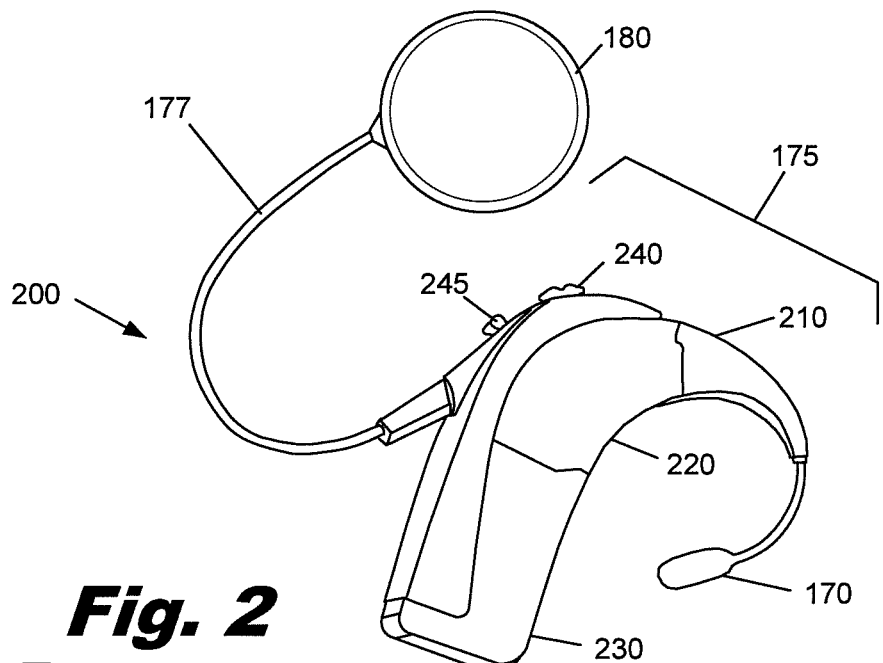
FIG. 2 is a diagram showing external components of an illustrative cochlear implant system.

FIG. 2 is an illustrative diagram showing a more detailed view of the external components (200) of one embodiment of a cochlear implant system. External components (200) of the cochlear implant system include a BTE unit (175) which comprises a microphone (170), an ear hook (210), a speech processor (220), and a battery (230), which may be rechargeable. The microphone (170) picks up sound from the environment and converts it into electrical impulses. The speech processor (220) selectively filters and manipulates the electrical impulses and sends the processed electrical signals through a cable (177) to the transmitter (180). A number of controls (240, 245) adjust the operation of the processor (220). These controls may include a volume switch (240) and program selection switch (245). The transmitter (180) receives the processed electrical signals from the processor (220) and transmits these electrical signals and power from the battery (230) to the internal components of the cochlear implant by electromagnetic induction, radio frequencies, optical communication, or any other wireless communication technology.

Figure 3:
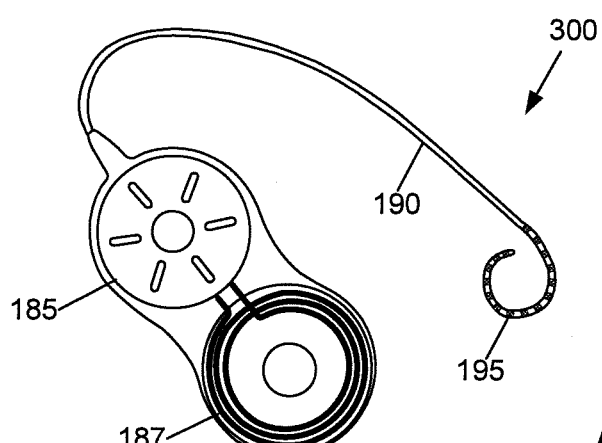
FIG. 3 is a diagram showing the internal components of an illustrative cochlear implant system.

FIG. 3 is an illustrative diagram showing the internal components (300) of one embodiment of a cochlear implant. These internal components (300) include an internal processor (185), an antenna (187), a cochlear lead (190), and an electrode array (195). The internal components (300) of the cochlear implant are surgically implanted such that the electrode array (195) is internal to the cochlea, as shown in FIG. 1. The internal processor (185) and antenna (187) are secured beneath the user's skin, typically above and behind the external ear, with the cochlear lead (190) connecting the internal processor (185) to the electrode array (195) within the cochlea. As discussed above, the antenna (187) receives signals from the transmitter (180) and sends the signals to the internal processor (185). The internal processor (185) modifies the signals and passes them through the cochlear lead (190) to the electrode array (195). The electrode array (195) is wound through the cochlea and provides direct electrical stimulation to the auditory nerves inside the cochlea. This provides the user with sensory input that is a representation of external sound waves which were sensed by the microphone (170).

Figure 4:
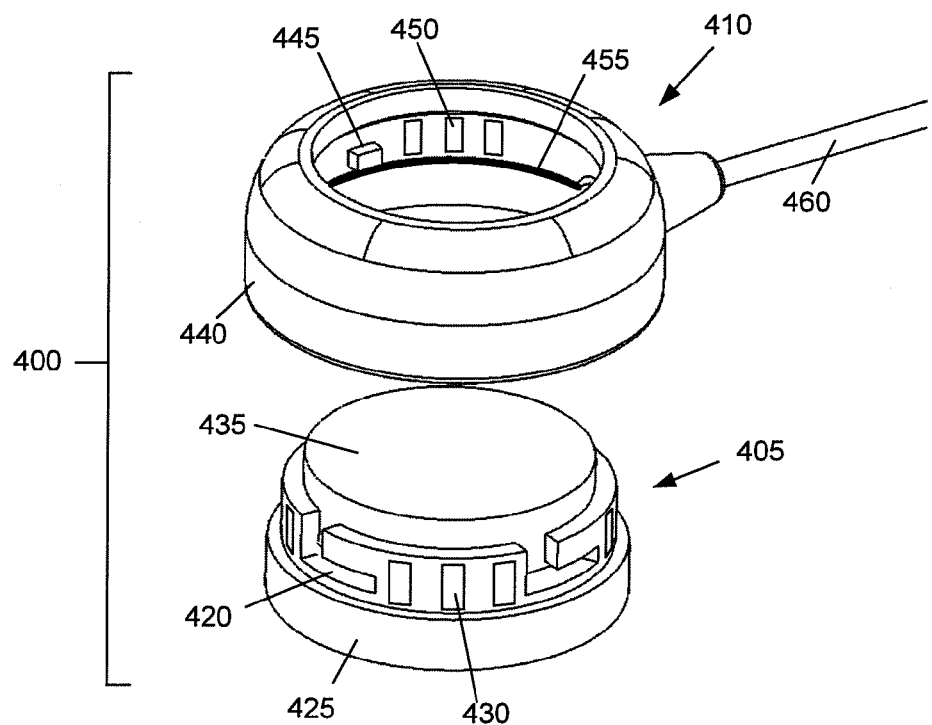
FIG. 4 is a perspective view of an illustrative modular speech processor headpiece, according to one embodiment of principles described herein.

FIG. 4 is a perspective view of an illustrative modular speech processor headpiece (400). According to one illustrative embodiment, the modular speech processor (400) includes a core (405) and a modular ring (410). The core (405) contains all of the external electronics. For example, the core (405) includes the microphone (170, FIG. 2), transmitter (180, FIG. 2), and the electronics contained within the processor (220, FIG. 2), such as power conditioning electronics, signal processors, filters, amplifiers, receivers, switches, memory, and other electronics. The base (425) of the core (405) may be substantially hollow to receive the electronics.

Additionally, the base (425) may contain a magnet or magnetic material which is attracted to a magnet or magnetic material within the antenna (187, FIG. 3). The attraction between the base (425) and the antenna (187, FIG. 3) holds the headpiece (400) in place over the antenna (187, FIG. 3).

The upper surface (435) may contain various elements such as microphone ports and visual indicators. According to one embodiment, a microphone port allows for a microphone within the core (405) to sense sound pressure waves. Various visual indicators, such as one or more light emitting diodes, could also be included on the upper surface (435) to communicate information regarding the function of both internal and external components of the cochlear implant system, such as battery status, the selected program, sensitivity or volume information, and communication status between the headpiece and internal processor (185, FIG. 3).

According to one embodiment, the core (405) is configured to receive various modular rings. In this illustrative embodiment, the modular rings may connect to core (405) by sliding tabs into slots (420) and then rotating the modular ring about the core (405) to lock the modular ring into place. The core (405) may contain a number of electrical contacts (430) which engage with matching electrical contacts on a modular ring, thereby allowing for electrical power and/or signals to be transmitted between the modular ring the core (405).

According to one embodiment, the modular ring (410) includes a housing (440) and a cable (460) connected to the housing (440). On the inner surface of the modular ring (410), a number of tabs (445) are configured to be received by the corresponding slots (420) in the core (405). Similarly, a number of contacts (450) on the inner surface of the modular ring (410) are configured to make electrical contact with the contacts (430) on the outer surface of the core (405). According to one embodiment, the modular ring (410) may also contain a number of o-rings (455) which seal against one or more surfaces of the core (405) to prevent contaminants from interfering with the electrical connections or otherwise disrupting the function of the core (405) and modular ring (410).

When the modular ring (410) includes a cable (460), the modular ring (410) may be attached to the core (405) for programming, to provide access to a long term power source, and/or to allow the user to access various accessories such as an external microphone, Bluetooth® receiver, or other accessories. For example, during programming or fitting the device by an audiologist, a corded modular ring (410) could be attached to the core (405) and connected to a programming computer. Additionally, a corded modular ring (410) may allow the user to access various conventional battery sources such as a battery pack. By accessing an external power source through the corded modular ring (410), the size and weight of the headpiece can be minimized. Additionally, the external power source may have increased battery capacity when compared with conventional BTE units.

Figure 5:
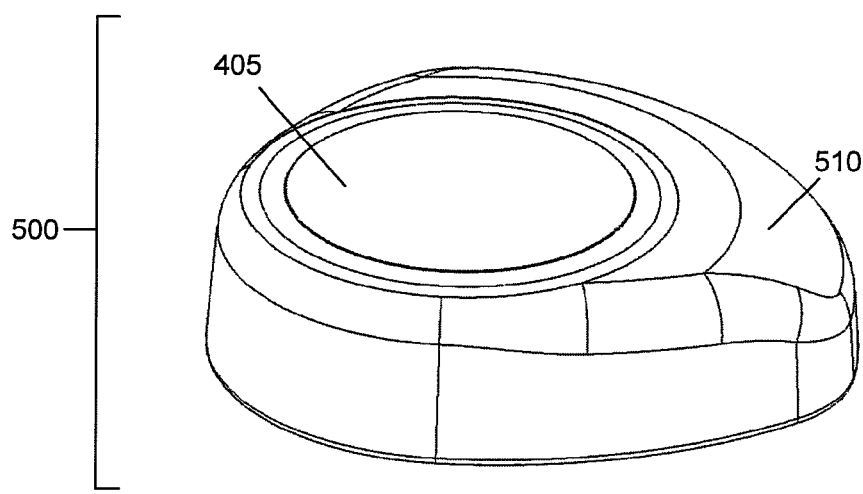
FIG. 5 is a perspective view of an illustrative modular speech processor headpiece, according to one embodiment of principles described herein.

In other situations, a modular ring that includes cable may not be the most desirable configuration. The modular nature of the core allows for any one of a number of alternative modular rings or other modular components to be attached to the core. FIG. 5 is a perspective view of an illustrative modular speech processor headpiece (500) in which the power source is integrated into a modular ring (510). As described above, the modular ring (510) fits over and around the core device and rotates to a locked position for security. In addition, the ring-to-core connection may provide a waterproof seal.

By way of example and not limitation, the modular ring (510) may contain a number of power sources, such as conventional lithium ion batteries, polymer lithium batteries, or zinc air batteries. Polymer lithium batteries operate using the same chemistry as conventional lithium ion batteries but contain the lithium-salt electrolyte within a solid polymer composite rather than a rigid metal case. Consequently, polymer lithium batteries can be lighter, more energy dense, and less vulnerable to physical damage. Further, polymer lithium batteries can be specifically shaped to fit the device it will power. Zinc air batteries operate by the oxidation of zinc with atmospheric oxygen. Zinc air batteries have high energy densities and are relatively inexpensive to produce. However, to operate, zinc air batteries must have direct exposure to the atmosphere which creates challenges in using these batteries in sealed systems.

Additionally or alternatively, the modular ring may contain any of a number of alternative accessories, such as radio frequency (RF) receivers or Bluetooth® receivers. These accessories can directly link the cochlear implant system to sound sources, reducing interference by other noise sources. For example, in an educational setting, teacher may wear a wireless microphone which transmits the teacher's voice over a radio frequency directly to a receiver contained within the modular ring. Similarly, a Bluetooth® receiver could be connected to a stereo, cell phone, or other audio source.

Figure 6:
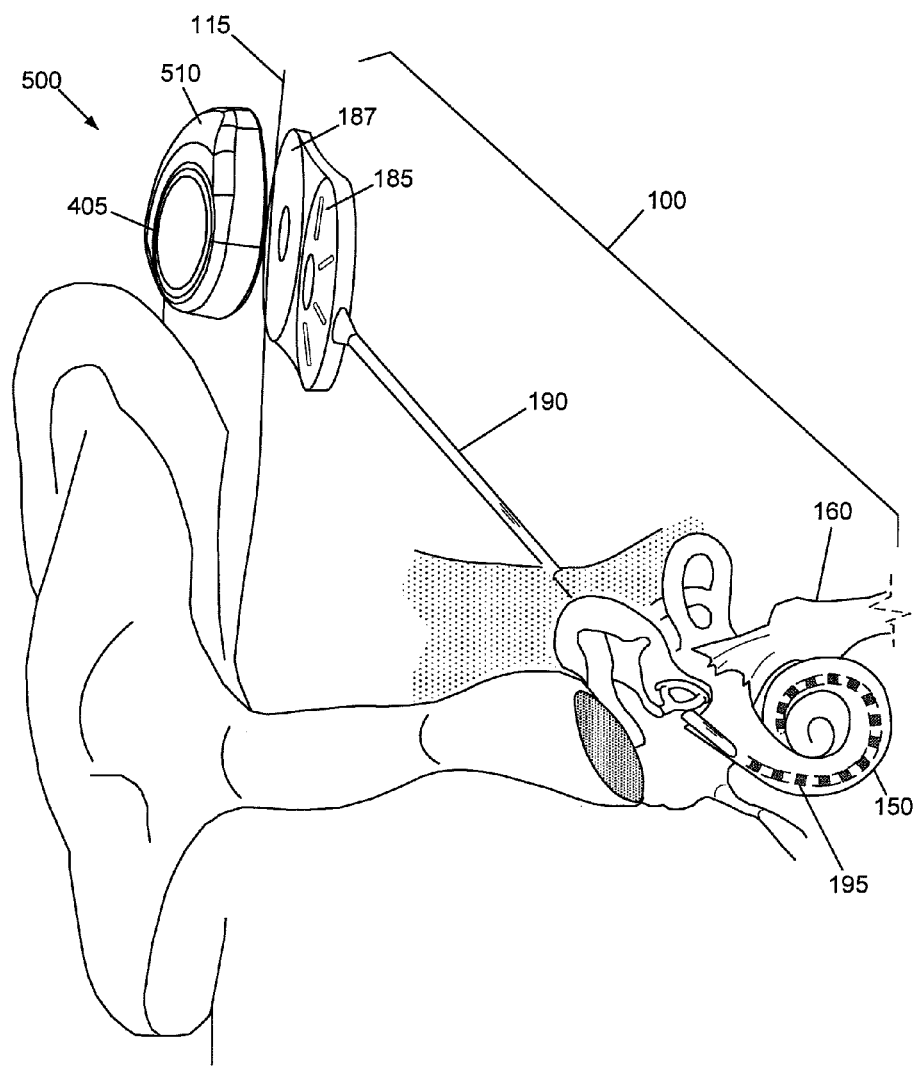
FIG. 6 is an illustrative diagram showing an illustrative modular speech processor headpiece interfacing with internal components of a cochlear implant system, according to one embodiment of principles described herein.

FIG. 6 is a diagram showing an illustrative modular speech processor headpiece (500) interfacing with internal components of a cochlear implant system. As mentioned above, the modular speech processor headpiece (500) may contain a core (405) and a modular ring (510) that contains a battery power source. This configuration consolidates all of the external components of the cochlear implant system into a single modular speech processor headpiece (500). This eliminates cables connecting the components together and the associated problems of routing the cables through clothing or the cable being snagged, pulled on, or tangled, causing the headpiece to fall off. Additionally, the modular speech processor headpiece (500) is more discrete than systems with multiple components. For example, the modular speech processor (500) may be completely covered by the user's hair or hat. Further, the modular speech processor headpiece (500) may be more robust than multiple component configurations. The modular speech processor headpiece (500) is easier to seal and eliminates cables which are susceptible to failure.

Figure 7:
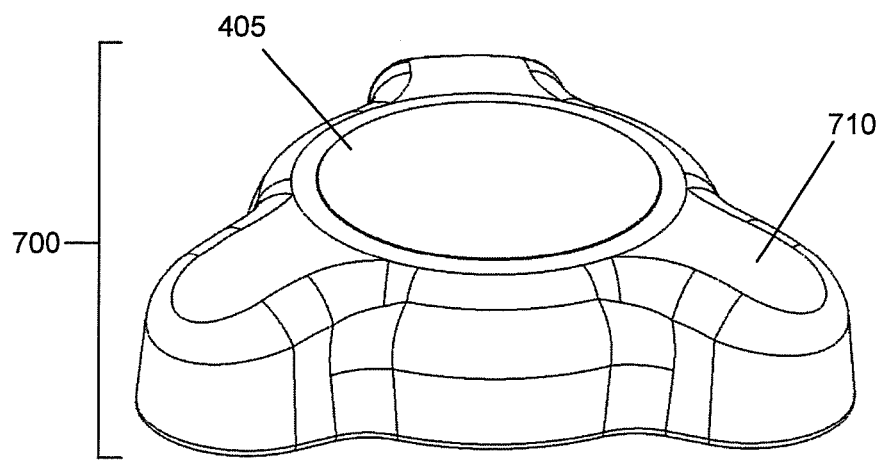
FIG. 7 is a perspective view of an illustrative modular speech processor headpiece, according to principles described herein.

A number of alternative embodiments can be created by attaching various modular rings to the core. FIG. 7 is a perspective view of an illustrative modular speech processor headpiece (700) in which a modular ring (710) is attached to the core (400). According to one exemplary embodiment, the modular ring (710) has a number of lobes, each of which is configured to receive a one or more button batteries. In an alternative embodiment, a lithium polymer battery can be shaped to be received by the modular ring (710).

In a number of illustrative embodiments described above, the top and bottom surfaces of the core (405) are exposed. There are a number of advantages to exposing the top and bottom of the core (405). For example, the core (405) can be manipulated by grasping the exposed top and bottom of the core (405), for example, between a thumb and forefinger. This allows the core (405) to be easily grasped and rotated to attach or detach the modular ring (410, 510, 710). The top and bottom of the core (405) may have a number of features or characteristics which facilitate grasping and manipulating the core (405). By way of example and not limitation, the top and/or bottom of the core (405) may be textured or contoured to provide a better gripping surface.

Additionally, there may also be a number of other functional advantages to exposing the top and bottom of the core (405). By exposing all or a portion of the top surface of the core, visual indicators can be placed on the top surface of the core (405). These visual indicators may communicate the status of the cochlear implant or attached battery. The top surface of the core (405) may also have a microphone port which needs to have a direct channel to the exterior environment. By exposing the bottom portion of the core, the transmitter within the core can better communicate with the underlying antenna.

The modular ring configurations described above are only one illustrative embodiment of modular components which connect to a core. There are a variety of other configurations which provide modularity and customization of a cochlear implant. By way of example and not limitation, a variety of modular components may be attached to the core without entirely enclosing the perimeter of the core.

Figure 8A:
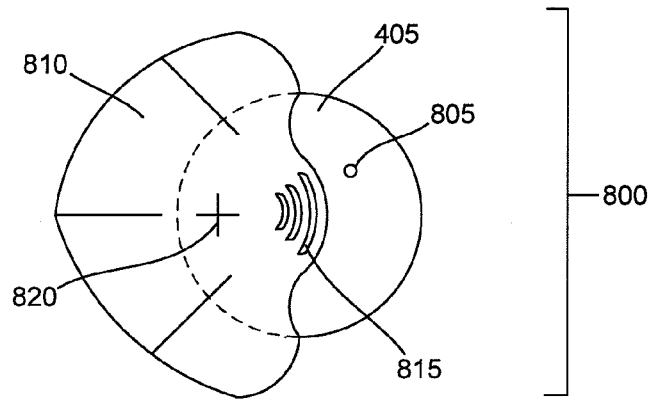
FIGS. 8A and 8B are a top and side view, respectively, of an illustrative modular speech processor headpiece, according to principles described herein.
Figure 8B:
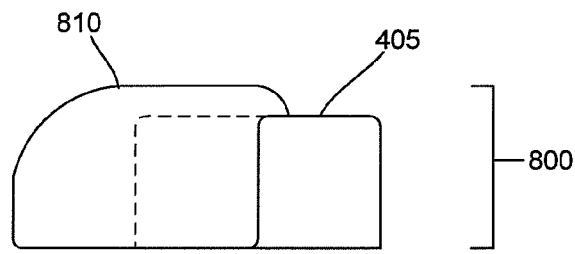

FIGS. 8A and 8B are a top view and a side view, respectively, of an illustrative modular speech processor headpiece (800) with an alternative geometry. Similar to other modular speech processor headpieces discussed above, this headpiece (800) combines all of the external components of a cochlear implant into a core (405). A modular component (810) attaches to one side of the core (405). The modular component (810) may serve a variety of functions, including providing power to the core (405). Additionally, the modular component (810) may contain a variety of receivers. By way of example and not limitation, a receiver within the modular component (810) may include Bluetooth®, radio frequency, 802.11, or other capabilities. The core (405) may also contain an internal microphone which accesses external sound waves through a microphone port (805).

The core (405) also includes an attachment means centered about the "+" (820). As previously mentioned, the attachment means may be made up of a magnetic attraction between a surgically implanted magnetic component and a second magnetic component within the core (405). For example, a magnet may be surgically implanted and a ferromagnetic material may be contained within the core (405) or vice versa. Additionally, two magnets may be used, one within the core (405) and one surgically implanted with the antenna (187, FIG. 3). When properly oriented, the use of two magnets can provide superior attractive force and/or allow the size of the magnetic components to be reduced.

To attach the headpiece (800), the headpiece (800) is simply brought into proximity with surgically implanted magnetic component. The attraction between the two magnetic components then centers the headpiece (800) over the antenna (187, FIG. 3) and holds the headpiece (800) in place.

The location of the attachment means can be positioned within the core (405) such that when the modular component (810) is attached to the core (405), the headpiece (800) is balanced about the attachment point (820). By balancing the headpiece (800) about the attachment point (820) (i.e. positioning the attachment point at the center of mass of the combined headpiece), the tendency of the headpiece (800) to rotate about the attachment point (820) when undergoing linear acceleration or vibration is significantly reduced or eliminated. By reducing the tendency of the headpiece (800) to rotate, the headpiece (800) becomes more comfortable to wear, especially for active individuals. Additionally, the abrasion of skin which is interposed between the headpiece (800) and the antenna (185, FIG. 6) can be reduced when the motion of the headpiece (800) is reduced.

The illustrative configuration shown in FIGS. 8A and 8B allows the core and the modular component to be easily grasped and manipulated during the assembly or disassembly of the core (405) and modular component (810). Portions of the upper and lower surfaces of the core (405) are exposed so that the core (405) can be grasped. The modular component can also be designed to be easily manipulated. According to one embodiment, the surfaces may be textured or contoured to provide additional friction between the surface and the user's fingers.

Figure 8C:
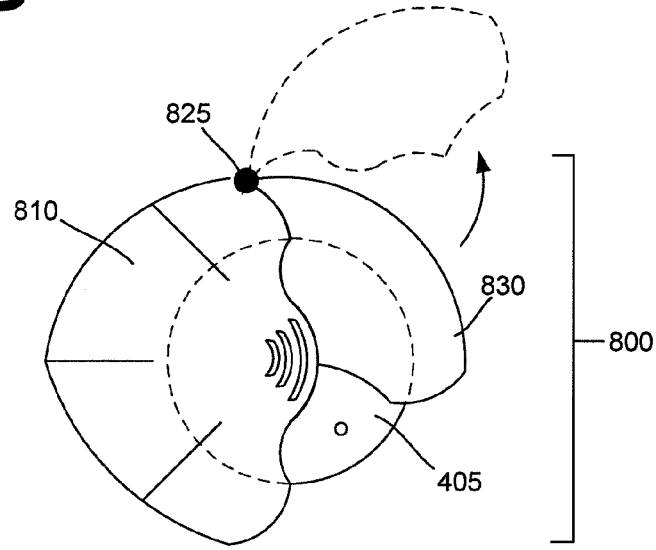
FIG. 8C is a top view of an illustrative modular speech processor headpiece showing the motion of a latching component, according to principles described herein.

FIG. 8C shows an illustrative embodiment of the headpiece (800) in which the modular component (810) may be provided with a hinge (825), which allows a latching component (830) to open, thereby releasing the core (405).

According to one embodiment, one or more indicators may be present on the modular component (810) or a surface of the core (405). By way of example and not limitation, the indicators may include light emitting diodes (815) which indicate the battery condition. For example, as the battery discharges, a light emitting diode is illuminated to indicate the need to recharge or replace the battery. This could be advantageous for a parent or teacher who can visually determine the battery level.

Similarly, the core unit may have one or more visual elements which indicate the state of the cochlear implant. For example, a light emitting diode could have a first color and illumination pattern which indicates that cochlear implant is operational. The light emitting diode could have a different color and/or illumination pattern for various malfunctions such as a malfunction of the core, lack of communication between the core and antenna, or an internal processor malfunction.

Figure 9A:
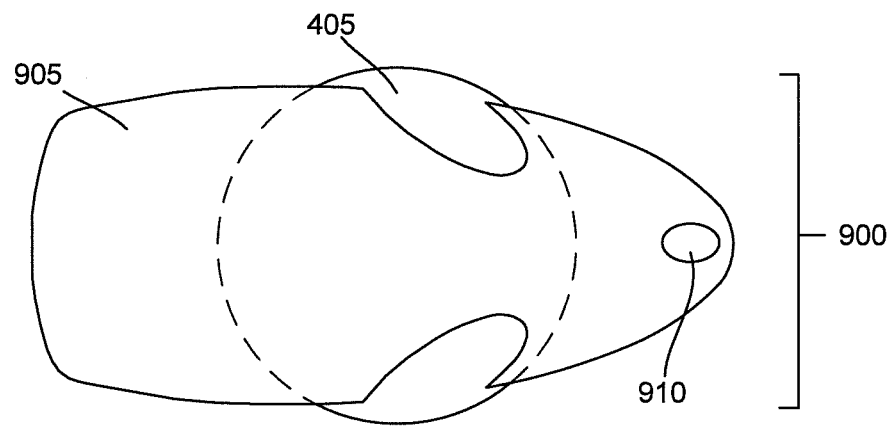
FIGS. 9A and 9B are a top and a side view, respectively of an illustrative modular speech processor headpiece, according to principles described herein.
Figure 9B:
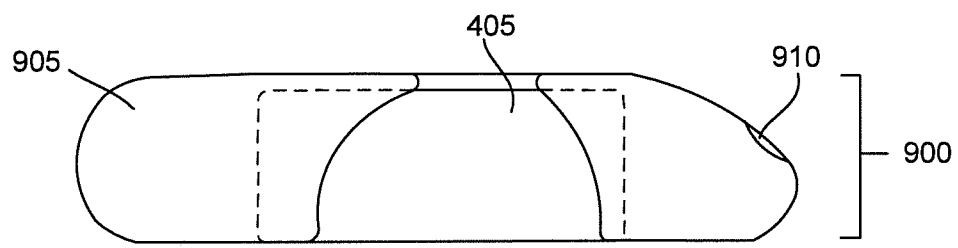

FIGS. 9A and 9B are a top view and a side view, respectively, of an illustrative modular speech processor headpiece (800) with an alternative geometry. In this illustrative embodiment, the core (405) is engaged on two sides by a modular component (905). The modular component (405) may attach in a variety of ways. For example, the core (405) may be simply snapped into the center of the modular component (905). In some illustrative embodiments, the core (405) may be keyed to ensure that the core (405) has the correct orientation with respect to the modular component (905).

To remove the core (405), the modular component (905) may be grasped in one hand and the core (405) removed with the opposite hand. The exposed portions of core (405) allow the user to grasp the core (405) by the sides and/or top and bottom of the core (405). As mentioned above, the core surfaces may be textured and/or contoured to provide a better gripping surface.

The modular component (905) may be balanced such that the center of mass of the modular component (905) aligns with the center of mass of the core (405). By aligning the center of mass of the modular component (905) with the center of mass of the core (405), the tendency for the headpiece (900) to rotate during acceleration or vibration can be reduced.

As previously discussed, a number of receivers, microphones, and battery technologies could be incorporated into the modular component (905). The modular component (905) and/or core (405) may contain a number of features including microphone ports, visual indicators, and other features. For example, although an omnidirectional microphone is generally preferred, the modular component (905) could additionally contain a directional microphone (910). The directional microphone (910) can be used by the patient to selectively amplify selected sound sources and to reduce undesirable background noise. According to one embodiment, the directional microphone (910) may be pointing in the same direction the patient is looking. For example, a patient may simply turn his head toward one who is speaking to point the directional microphone (910) in the speaker's direction to preferentially sense his voice.

The modular speech processor headpiece can allow for any of a number of modular components to be attached to the processor. For example, the patient may have two or more modular components. While one modular component is providing power to the cochlear implant, the other modular component can be recharging its battery. Additionally or alternatively, the functionality provided by different modular components may be different. The user can select the modular component that is most appropriate for the situation. For example, during a social event, the user may select a modular component that is less obtrusive or complements other clothing accessories. During the course of a normal day, the user may select a modular component with a longer lifetime or with a needed receiver. For example, if the user attends school, the user may need a battery that can supply power throughout the school day and a receiver that can receive amplified/filtered signals from a wireless microphone worn by the teacher.

In sum, a modular speech processor headpiece combines the external components of the cochlear implant system into a single unit that is worn directly over the surgically implanted antenna. This eliminates the need for a separate body worn processor or BTE processor and the connecting cable. Consequently, the modular speech processor headpiece reduces the complexity of wearing and using a cochlear implant. The modular speech processor headpiece eliminates the need to route a cable through clothing or hair and the possibility of snagging a cable. Additionally, the modular speech processor headpiece can be more robust, modular, and significantly less visually intrusive than processors of conventional cochlear implant systems.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. A modular headpiece for use with a cochlear implant, the modular headpiece comprising:
   a core, having a top surface and a bottom surface, in which a sound processor and a transmitter that transmits signals to the cochlear implant are located, and including a magnet that is attracted to the cochlear implant; and
   a detachable modular component configured to releasably engage the core and to supply electrical power to the core;
   wherein the core and the detachable modular component are respectively configured such that, when the detachable modular component engages the core, the modular headpiece defines a bottom surface that faces the cochlear implant to which the magnet is attracted and a top surface that faces away from the cochlear implant to which the magnet is attracted, the bottom surface of the core defines at least a portion of the bottom surface of the modular headpiece, and the detachable modular component defines at least a portion of the top surface of the modular headpiece.

2. A modular headpiece as claimed in claim 1, wherein the core includes a microphone that is operably connected to the sound processor.

3. A modular headpiece as claimed in claim 1, wherein
the core defines an outer surface and includes a plurality of core electrical contacts disposed about the outer surface;
the detachable modular component defines an inner surface and includes a plurality of component electrical contacts disposed about the inner surface; and
electrical contact is established between the core electrical contacts and the component electrical contacts when the detachable modular component engages the core.

4. A modular headpiece as claimed in claim 1, wherein the detachable modular component includes a power storage device.

5. A modular headpiece as claimed in claim 1, wherein the detachable modular component includes a wired interface.

6. A modular headpiece as claimed in claim 1, wherein the detachable modular component includes a wireless receiver.

7. A modular headpiece as claimed in claim 1, wherein the detachable modular component includes a microphone.

8. A modular headpiece for use with a cochlear implant, the modular headpiece comprising:
a core including
a single common housing,
a microphone, a sound processor that processes signals from the microphone, and a transmitter that transmits processed signals to the cochlear implant, wherein the microphone, the sound processor and the transmitter are located within the single common housing,
a core electrical connector, and
a magnet that is attracted to the cochlear implant; and
a detachable modular component including a component electrical connector and configured to engage the core such that an electrical connection is made between the core electrical connector and the component electrical connector when the detachable modular component engages the core.

9. A modular headpiece for use with a cochlear implant, the modular headpiece comprising:
a core, having a top surface and a bottom surface, in which a sound processor and a transmitter that transmits signals to the cochlear implant are located; and
a detachable modular ring configured to releasably engage the core, such that at least a portion of the core bottom surface is not covered by the modular component, and to supply electrical power to the core, and that, when attached to the core, circumscribes the core.

10. A modular headpiece as claimed in claim 8, wherein
the core electrical connector includes a first plurality of electrical contacts;
the component electrical connector includes a second plurality of electrical contacts; and
an electrical connection is made between at least some of the first plurality of electrical contacts and at least some of the second plurality of electrical contacts when the detachable modular component engages the core.

11. A modular headpiece as claimed in claim 8, wherein the detachable modular component comprises a plurality of detachable modular components.

12. A modular headpiece as claimed in claim 11, wherein each of the detachable modular components is configured to at least one of: supply power to the core, receive wireless signals, supply additional processing capability, connect the core to a programmer, provide an interface for a wired connection, and change the external appearance of the modular headpiece.

13. A modular headpiece as claimed in claim 11, wherein the respective configurations of the core and the detachable modular components are such that only one of the detachable modular components can engage the core at a time.

14. A modular headpiece for use with a cochlear implant, the modular headpiece comprising:
a cylindrically shaped core including
a single common housing,
a microphone, a sound processor that processes signals from the microphone, and a transmitter that transmits processed signals to the cochlear implant, wherein the microphone, the sound processor and the transmitter are located within the single common housing, and
a core electrical connector; and
an annularly shaped detachable modular component including a component electrical connector and configured to receive and engage the cylindrically shaped core such that an electrical connection is made between the core electrical connector and the component electrical connector when the detachable modular component engages the core.

15. A modular headpiece as claimed in claim 14, wherein
the core defines an outer perimeter and includes a plurality of slots disposed around the outer perimeter; and
the detachable modular component defines an inner perimeter and includes a plurality of tabs disposed around the inner perimeter that are configured to be received by the plurality of slots.

16. A modular headpiece for use with a cochlear implant, the modular headpiece comprising:
a core including
a single common housing,
a microphone, a sound processor that processes signals from the microphone, and a transmitter that transmits processed signals to the cochlear implant, wherein the microphone, the sound processor and the transmitter are located within the single common housing, and
a core electrical connector; and
a detachable modular component including a component electrical connector and configured to engage the core such that an electrical connection is made between the core electrical connector and the component electrical connector when the detachable modular component engages the core, the detachable modular component further including a waterproof seal positioned such that it will be located between the core and detachable modular component when the detachable modular component engages the core.

17. A modular headpiece for use with a cochlear implant, the modular headpiece comprising:
a core including
a core housing with a perimeter, an upper surface defined by the perimeter, and lower surface defined by the perimeter,
a microphone, a sound processor that processes signals from the microphone, and a transmitter that transmits processed signals to the cochlear implant, wherein the microphone, the sound processor and the transmitter are located within the core housing, a magnet that is attracted to the cochlear implant through the lower surface of the core housing, and
a core electrical connector;
a detachable power supply component, including a power storage device and a component electrical connector, and configured to engage the core such that an electrical connection is made between the core electrical connector and the component electrical connector when the detachable power supply component engages the core;
wherein the respective configurations of the core and the detachable power supply component are such that, when engaged with one another, the core and the detachable power supply component together define a head-wearable device having a lower surface that faces the cochlear implant, the lower surface of the core housing defines at least a portion of the lower surface of the head-wearable device, and the detachable power supply component covers a portion of the upper surface of the core housing.

18. A modular headpiece as claimed in claim 17, wherein the detachable power supply component contains a plurality of batteries.

19. A modular headpiece as claimed in claim 17, wherein the core is cylindrically shaped; and
the detachable power supply component has an annular inner surface that is configured to receive the cylindrically shaped core.

20. A modular headpiece as claimed in claim 17, wherein the detachable power supply component includes a semi-circular indentation that is configured to receive a portion of the core.

21. A modular headpiece as claimed in claim 17, wherein the detachable power supply component is configured to releasably engage the core such that the lower surface of the core housing is not covered by the detachable power supply component.

22. A modular headpiece for use with a cochlear implant, the modular headpiece comprising:
a core, including a single common housing having a top surface and a bottom surface, in which a microphone, a sound processor and a transmitter that transmits signals to the cochlear implant are located; and
a detachable modular component that is rotatable relative to the core between a locked position, where the detachable modular component is locked to the core, and an unlocked position, where the detachable modular component is removable from the core;
wherein the core and the detachable modular component are respectively configured such that, when the detachable modular component is locked to the core, no portion of the core housing bottom surface is covered by the detachable modular component.

23. A modular headpiece as claimed in claim 22, wherein the detachable modular component comprises a ring that contains a plurality of batteries.

* * * * *